US00PP21242P2

(12) United States Plant Patent
Heuger

(10) Patent No.: US PP21,242 P2
(45) Date of Patent: Aug. 24, 2010

(54) ***HELLEBORUS* PLANT NAMED 'COSEH 230'**
(50) Latin Name: *Helleborus niger*
Varietal Denomination: COSEH 230

(76) Inventor: Josef Heuger, Postfach 11 03, D-49215 Glandorf (DE)

( * ) Notice: Subject to any disclaimer, the term of this patent is extended or adjusted under 35 U.S.C. 154(b) by 0 days.

(21) Appl. No.: 12/386,659

(22) Filed: Apr. 20, 2009

(51) Int. Cl.
*A01H 5/00* (2006.01)

(52) U.S. Cl. ..... Plt./439

(58) Field of Classification Search ..... Plt./439
See application file for complete search history.

*Primary Examiner*—Annette H Para
(74) *Attorney, Agent, or Firm*—C. A. Whealy

(57) ABSTRACT

A new and distinct cultivar of *Helleborus* plant named 'COSEH 230', characterized by its upright, outwardly spreading and mounded plant habit; freely flowering habit; long flowering period; and semi-double white-colored flowers.

1 Drawing Sheet

Botanical designation: *Helleborus niger.*
Cultivar denomination: 'COSEH 230'.

BACKGROUND OF THE INVENTION

The present invention relates to a new and distinct cultivar of *Helleborus* plant, botanically known as *Helleborus niger,* and hereinafter referred to by the name 'COSEH 230'.

The new *Helleborus* plant is a product of a planned breeding program in Glandorf, Germany. The objective of the breeding program was to create new uniform *Helleborus* cultivars with unique and attractive flower coloration and resistance to pests.

The new *Helleborus* plant originated from a cross-pollination conducted by the Inventor in Glandorf, Germany in November, 2002 of an unnamed proprietary seedling selection of *Helleborus niger,* not patented, as the female, or seed, parent with an unnamed proprietary seedling selection of *Helleborus niger,* not patented, as the male, or seed, parent. The new *Helleborus* plant was discovered and selected by the Inventor as a single flowering plant from within the progeny of the stated cross-pollination grown in a controlled greenhouse environment in Glandorf, Germany in February, 2005.

Asexual reproduction of the new *Helleborus* plant by divisions in a controlled greenhouse environment in Glandorf, Germany since March, 2005, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'COSEH 230'. These characteristics in combination distinguish 'COSEH 230' as a new and distinct cultivar of *Helleborus:*

1. Upright, outwardly spreading and mounded plant habit.
2. Freely flowering habit.
3. Long flowering period.
4. Semi-double white-colored flowers.

Compared to plants of the parent selections, plants of the new *Helleborus* are more uniform and more freely flowering.

Plants of the new *Helleborus* can be compared to plants of *Helleborus niger* 'HGC Josef Lemper', disclosed in U.S. Plant Pat. No. 15,615. Plants of the new *Helleborus* differ primarily from plants of 'HGC Josef Lemper' in the following characteristics:

1. Plants of the new *Helleborus* have darker green-colored leaves than plants of 'HGC Josef Lemper'.
2. Plants of the new *Helleborus* flower later than plants of 'HGC Josef Lemper'.
3. Plants of the new *Helleborus* have semi-double flowers whereas plants of 'HGC Josef Lemper' have single flowers.

BRIEF DESCRIPTION OF THE PHOTOGRAPH

The accompanying colored photograph illustrates the overall appearance of the new *Helleborus* plant, showing the colors as true as it is reasonably possible to obtain in colored reproductions of this type. Colors in the photograph may differ slightly from the color values cited in the detailed botanical description which accurately describe the colors of the new *Helleborus* plant. The photograph comprises a side perspective view of a typical flowering plant of 'COSEH 230' grown in a container.

DETAILED BOTANICAL DESCRIPTION

The aforementioned photograph and following observations, measurements and values describe plants grown in Glandorf, Germany in 15-cm containers during the winter in an outdoor nursery and under conditions which closely approximate commercial *Helleborus* production. During the production of the plants, day temperatures ranged from 5° C. to 32° C. and night temperatures ranged from 1° C. to 25° C. Plants were one year old when the photograph and the description were taken. In the following description, color references are made to The Royal Horticultural Society Colour Chart, 2001 and 2007 Editions, except where general terms of ordinary dictionary significance are used.

Botanical classification: *Helleborus niger* 'COSEH 230'.

Parentage:

*Female, or seed, parent.*—Unnamed proprietary seedling selection of *Helleborus niger,* not patented.

*Male, or pollen, parent.*—Unnamed proprietary seedling selection of *Helleborus niger,* not patented.

Propagation:

*Type.*—By divisions.

*Time to initiate roots.*—About 60 days at 12° C.

*Time to produce a rooted young plant.*—About six months at 4° C. to 15° C.

*Root description.*—Thick to thin, fleshy; white to brown in color.

*Rooting habit.*—Sparse.

Plant description:

*Plant form and growth habit.*—*Herbaceous* perennial; upright, outwardly spreading and mounded plant habit; vigorous growth habit.

*Plant height, to top of flowers.*—About 20 cm to 25 cm.

*Plant height, to top of foliar plane.*—About 10 cm to 15 cm.

*Plant diameter* (*area of spread*).—About 30 cm to 35 cm.

Foliage description:

*Arrangement.*—Palmately compound with five to seven leaflets per leaf.

*Leaf length.*—About 5.5 cm to 8 cm.

*Leaf width.*—About 2.5 cm to 5 cm.

*Leaflet shape.*—Pedate.

*Leaflet apex.*—Broadly acuminate.

*Leaflet base.*—Asymmetrically acute.

*Leaflet margin.*—Serrate to entire.

*Leaflet texture, upper and lower surfaces.*—Smooth, glabrous; leathery.

*Leaflet venation pattern.*—Pinnate; reticulate.

*Leaflet color.*—Developing leaves, upper surface: Close to 137C. Developing leaves, lower surface: Close to 148A to 148B. Fully developed leaves, upper surface: Close to 137A; venation, close to 146B. Fully developed leaves, lower surface: Close to 147C; venation, close to 146C to 146D, mid-vein occasionally overlain with close to 166A.

*Petiole.*—Length: About 5 mm to 15 mm. Diameter: About 3 mm. Texture, upper and lower surfaces: Smooth, glabrous. Color, upper and lower surfaces: Close to 146B; occasional and random spots, close to 166A.

Flower description:

*Flower shape and habit.*—Semi-double rotate flowers; freely flowering habit, about 10 to 15 flowers developing per plant. Petals not observed.

*Fragrance.*—Slightly fragrant, pleasant.

*Natural flowering season.*—Long flowering period; plants flower from January to March in Germany.

*Flower longevity on the plant.*—About three to four months; flowers persistent.

*Flower buds.*—Length: About 1 cm to 2 cm. Diameter: About 1 cm to 1.2 cm. Shape: Ovoid. Color: Close to 145C to 145D.

*Flowers.*—Diameter: About 6 cm to 7 cm. Depth (height): About 2 cm to 3 cm.

*Sepals.*—Arrangement: About seven in a single outer whorl and about 25 smaller sepals interior to the outer whorl. Length, outer sepals: About 3 cm to 4 cm. Length, inner sepals: About 1.5 cm to 2.5 cm. Width, outer sepals: About 2 cm to 3 cm. Width, inner sepals: About 9 mm to 13 mm. Shape, outer sepals: Broadly ovate. Shape, inner sepals: Oval. Apex, all sepals: Rounded. Base, outer sepals: Obtuse. Base, inner sepals: Obtuse or fused. Margin, all sepals: Entire. Texture, all sepals, upper and lower surfaces: Smooth, glabrous; satiny. Color, all sepals: When opening, upper and lower surfaces: Close to N155D. Fully opened, upper and lower surfaces: Close to N155D; color becoming closer to 145A to 145B with development.

*Peduncles.*—Strength: Strong. Length: About 20 cm. Diameter: About 4 mm to 8 mm. Aspect: Mostly upright. Texture: Smooth, glabrous. Color: Close to 145A; random blotches, close to 183A.

*Reproductive organs.*—Stamens: Quantity per flower: About 100. Anther shape: Elliptical. Anther length: About 1 mm. Anther color: Close to 3B. Pollen amount: None observed. Pistils: Quantity per flower: About eight. Pistil length: About 1.3 cm. Stigma shape: Pointed. Stigma color: Close to 145C. Style length: About 5 mm. Style color: Close to 145C. Ovary color: Between 145C and 150C. Nectaries: None observed. Seeds/fruits: Seed and fruit development have not been observed.

Garden performance: Plants of the new *Helleborus* have been observed to have good garden performance and to tolerate rain, wind and temperatures from about −10° C. to about 36° C.

Pathogen/pest resistance: Plants of the new *Helleborus* have not been shown to be resistant to pathogens and pests common to *Helleborus.*

It is claimed:

1. A new and distinct *Helleborus* plant named 'COSEH 230' as illustrated and described.

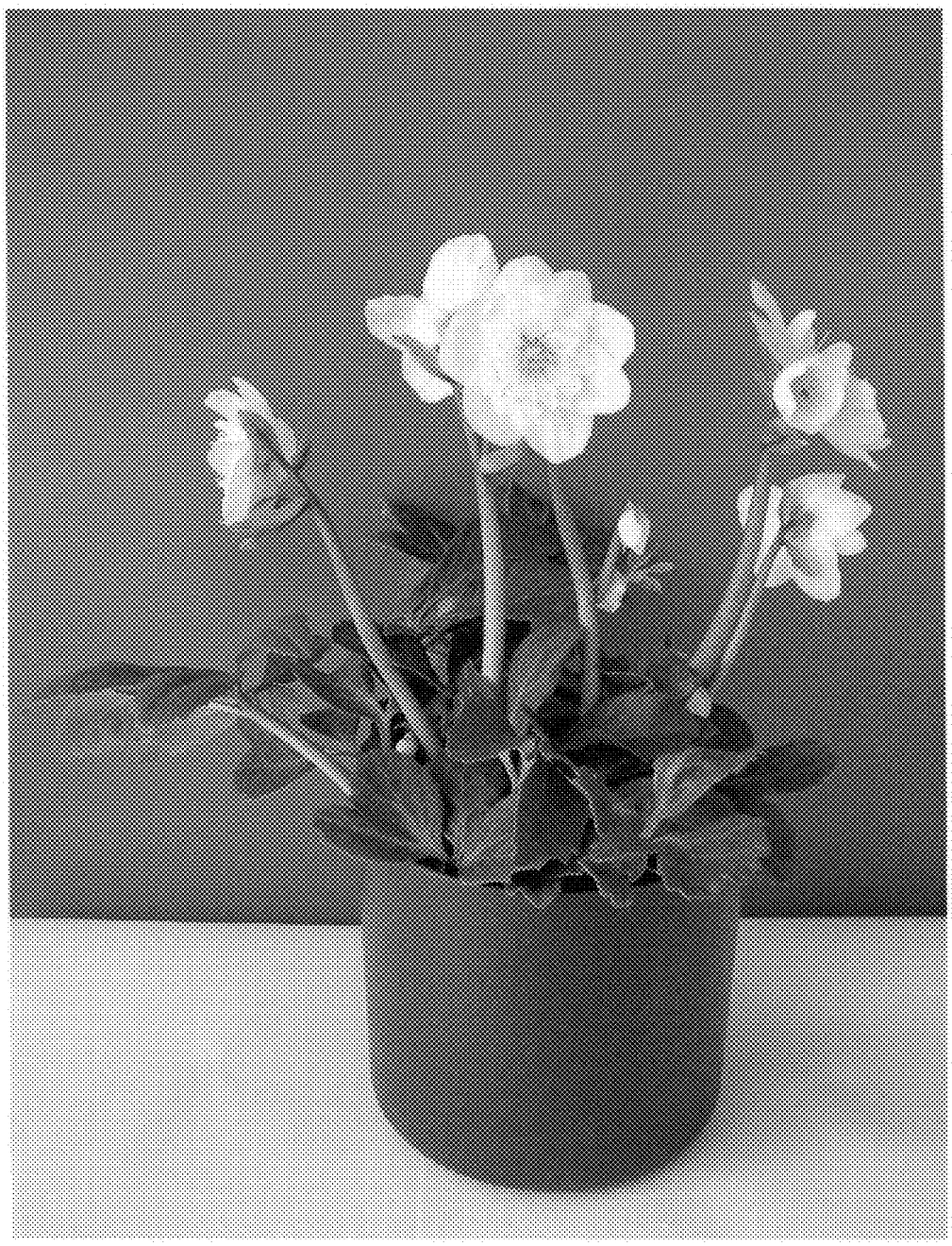

* * * * *